US012733793B2

(12) United States Patent
Watanabe

(10) Patent No.: US 12,733,793 B2
(45) Date of Patent: Sep. 15, 2026

(54) ENDOSCOPE SYSTEM

(71) Applicant: OLYMPUS CORPORATION, Tokyo (JP)

(72) Inventor: Tadashi Watanabe, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 564 days.

(21) Appl. No.: 18/295,499

(22) Filed: Apr. 4, 2023

(65) Prior Publication Data

US 2023/0233061 A1 Jul. 27, 2023

Related U.S. Application Data

(63) Continuation of application No. PCT/JP2021/007359, filed on Feb. 26, 2021.

(51) Int. Cl.
*A61B 1/00* (2006.01)
*A61B 1/005* (2006.01)
(Continued)

(52) U.S. Cl.
CPC ...... *A61B 1/00097* (2022.02); *A61B 1/00006* (2013.01); *A61B 1/00045* (2013.01); *A61B 1/00055* (2013.01); *A61B 1/0052* (2013.01); *A61B 1/009* (2022.02); *A61B 1/018* (2013.01); *A61B 1/2736* (2013.01)

(58) Field of Classification Search
CPC ............ A61B 1/00097; A61B 1/00045; A61B 1/00055; A61B 1/009; A61B 2034/2061; A61B 1/00006; A61B 1/0051–0056
See application file for complete search history.

(56) References Cited

U.S. PATENT DOCUMENTS 4,292,961 A * 10/1981 Kawashima ....... A61B 1/00097
600/117
2002/0183592 A1 12/2002 Suzuki et al.
(Continued)

FOREIGN PATENT DOCUMENTS

CN 103068297 A 4/2013
CN 106913312 A 7/2017
(Continued)

OTHER PUBLICATIONS

Chinese Office Action dated Jul. 11, 2025 received in 202180070320.2.

(Continued)

*Primary Examiner* — Aaron B Fairchild
(74) *Attorney, Agent, or Firm* — Scully, Scott, Murphy & Presser, P.C.

(57) ABSTRACT

An endoscope system includes: an endoscope including an insertion portion configured to be inserted into a subject; a distance measurement unit configured to measure a distance between the insertion portion and an object by transmitting and receiving millimeter waves or submillimeter waves; and a flexible waveguide that has one end that is connected to the distance measurement unit and another end that is exposed to outside from a distal end of the insertion portion, the flexible waveguide being configured to propagates the millimeter waves or submillimeter waves transmitted and received by the distance measurement unit.

9 Claims, 5 Drawing Sheets

(51) Int. Cl.
*A61B 1/018* (2006.01)
*A61B 1/273* (2006.01)

(56) References Cited

U.S. PATENT DOCUMENTS

| | | | |
|---|---|---|---|
| 2011/0073114 A1 | 3/2011 | Su | |
| 2012/0283555 A1 | 11/2012 | Su | |
| 2013/0096423 A1 | 4/2013 | Yamamoto et al. | |
| 2018/0136456 A1* | 5/2018 | Watanabe | H04N 7/22 |
| 2018/0338670 A1 | 11/2018 | Yamaguchi et al. | |

FOREIGN PATENT DOCUMENTS

| | | | | |
|---|---|---|---|---|
| JP | H10-272088 | * | 10/1998 | |
| JP | H10-272088 | A | 10/1998 | |
| JP | 2002355215 | A | 12/2002 | |
| JP | 2008122278 | * | 5/2008 | G01N 21/35 |
| JP | 2011227132 | A | 11/2011 | |
| JP | 2011234871 | A | 11/2011 | |
| JP | 2017-070523 | A | 4/2017 | |
| JP | 6205125 | B2 | 9/2017 | |
| JP | 2020-058524 | A | 4/2020 | |
| KR | 2016-0069622 | A | 6/2016 | |

OTHER PUBLICATIONS

Chinese Office Action dated Nov. 18, 2025 received in 202180070320.2.

International Search Report dated Apr. 13, 2021 received in PCT/JP2021/007359.

* cited by examiner

ENDOSCOPE SYSTEM

CROSS-REFERENCE TO RELATED APPLICATION

This application is a continuation of International Application No. PCT/JP2021/007359, filed on Feb. 26, 2021, the entire contents of which are incorporated herein by reference.

BACKGROUND

1. Technical Field

The disclosure relates to an endoscope system.

2. Related Art

An endoscope system including an endoscope that includes an insertion portion having a distal end in which an imaging unit is provided and that is inserted into a subject and a control device that processes an image signal from the imaging unit has been known (refer to Japanese patent No. 6205125).

In the endoscope system described in Japanese patent No. 6205125, an endoscope consists of a flexible endoscope whose insertion portion is flexible.

SUMMARY

In some embodiments, an endoscope system includes: an endoscope including an insertion portion configured to be inserted into a subject; a distance measurement unit configured to measure a distance between the insertion portion and an object by transmitting and receiving millimeter waves or submillimeter waves; and a flexible waveguide that has one end that is connected to the distance measurement unit and another end that is exposed to outside from a distal end of the insertion portion, the flexible waveguide being configured to propagates the millimeter waves or submillimeter waves transmitted and received by the distance measurement unit.

In some embodiments, an endoscope system includes: an endoscope including an insertion portion configured to be inserted into a subject; a detection unit configured to detect an abnormal site in the subject by transmitting and receiving millimeter waves or submillimeter waves; and a flexible waveguide that has one end that is connected to the detection unit and another end that is exposed to outside from a distal end of the insertion portion, the flexible waveguide being configured to propagate the millimeter waves or submillimeter waves transmitted and received by the detection unit.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
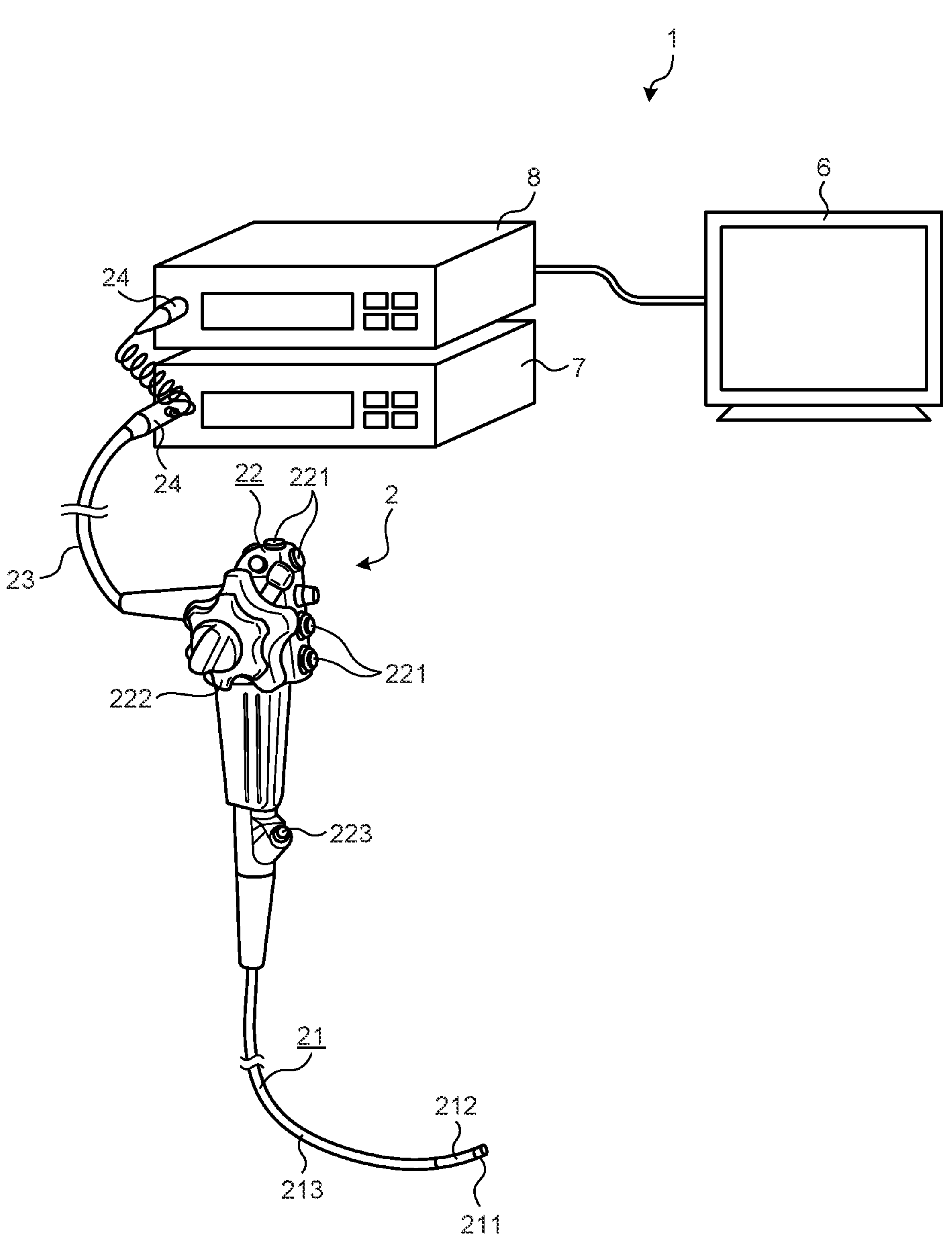
FIG. 1 is a diagram illustrating a configuration of an endoscope system according to a first embodiment.

With reference to the accompanying drawings, modes for carrying out the disclosure ("embodiments" below) will be described below. Note that the embodiments described below do not limit the disclosure. Furthermore, in the illustration of the drawings, the same parts are denoted with the same reference numerals.

First Embodiment

Configuration of Endoscope System

Figure 2:
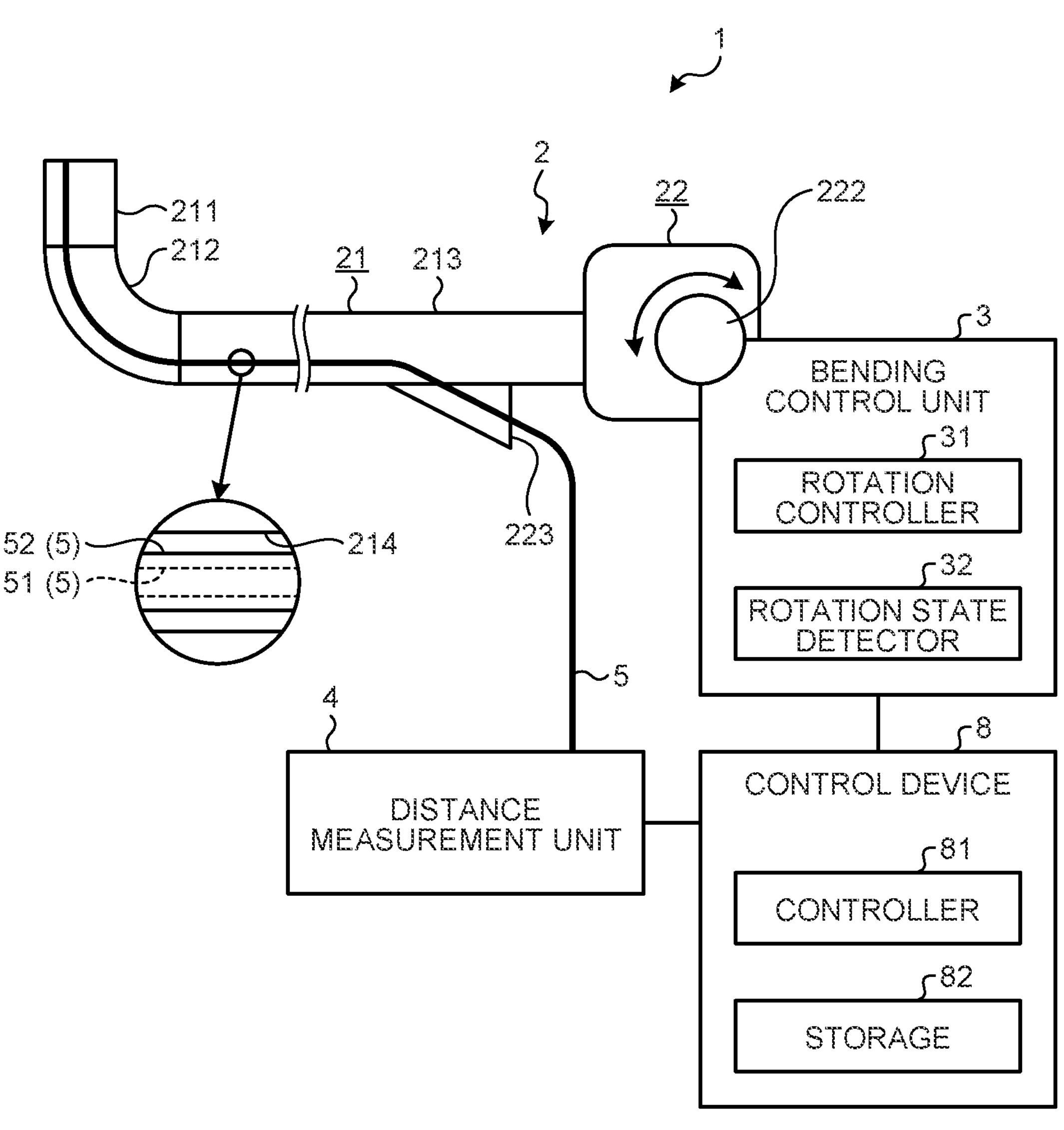
FIG. 2 is a diagram illustrating a configuration of a relevant part of the endoscope system.

FIG. 1 is a diagram illustrating a configuration of an endoscope system 1 according to a first embodiment. FIG. 2 is a diagram illustrating a configuration of a relevant part of the endoscope system 1.

The endoscope system 1 is a system that is used in, for example, medical fields and that observes an inside of a subject (an inside of a living body). As illustrated in FIG. 1 or FIG. 2, the endoscope system 1 includes an endoscope 2, a bending control unit 3 (FIG. 2), a distance measurement unit 4 (FIG. 2), a flexible waveguide 5 (FIG. 2), a display 6 (FIG. 1), a light source 7 (FIG. 1), and a control device 8.

The endoscope 2 is partly inserted into the living body, captures a subject image that is reflected from the inside of the living body, and outputs an image signal that is generated by the image capturing. As illustrated in FIG. 1, the endoscope 2 includes an insertion portion 21, an operation portion 22, a universal cord 23, and a connector 24.

The insertion portion 21 is a portion that is at least partly flexible and is inserted into the living body. As illustrated in FIG. 1 or FIG. 2, the insertion portion 21 includes a distal end unit 211, a bendable portion 212, and a flexible tube 213.

The distal end unit 211 is provided at a distal end of the insertion portion 21. Although specific illustration is omitted, the distal end unit 211 is provided with an illumination optical system, an imaging optical system, and an imaging unit.

The illumination optical system faces one end of a light guide (not illustrated in the drawing) that is drawn in the insertion portion 21 and applies light that is transmitted by the light guide to the inside of the living body from the distal end of the insertion portion 21.

The imaging optical system takes the light (the subject image) that is applied from the illumination optical system and that is reflected from the inside of the living body and forms an image on an imaging surface of an imaging device that constitutes the imaging unit.

The imaging unit includes the imaging device, such as a charge coupled device (CCD) or a complementary metal oxide semiconductor (CMOS), captures the subject image that is formed by the imaging optical system, and outputs the image signal that is generated by the image capturing.

The bendable portion 212 is coupled to a proximal end side (a side of the operation portion 22) of the distal end unit 211. The bendable portion 212 has a configuration in which, although specific illustration in the drawings is omitted, a plurality of bending pieces are coupled to each other and thus is bendable.

The flexible tube 213 is coupled to a proximal end side (a side of the operation portion 22) of the bendable portion 212 and has an elongated form that is flexible.

The operation portion 22 is connected to a proximal end portion of the insertion portion 21. The operation portion 22 receives various types of operations on the endoscope 2. As illustrated in FIG. 1 or FIG. 2, the operation portion 22 is provided with a plurality of operation parts 221, a knob 222, and an insertion port 223.

The operation parts 221 include a button that receives various types of operations, etc.

The knob 222 is rotatable according to a user operation. A rotation of the knob 222 causes a bendable mechanism (not illustrated in the drawings), such as a wire that is arranged in the insertion portion 21 and that is made of metal or resin, to operate. Accordingly, the bendable portion 212 bends.

The insertion port 223 communicates with a channel 214 (FIG. 2) extending from the distal end of the insertion portion 21. The insertion port 223 is an insertion opening via which a treatment tool (not illustrated in the drawings), such as a puncture needle, or the flexible waveguide 5 is inserted into the channel 214 from the outside of the channel 214.

The universal cord 23 extends from the operation portion in a direction different from a direction in which the insertion portion 21 extends. The universal cord 23 is a cord in which the above-described light guide, a signal line that transmits the above-described image signal, etc., are arranged.

The connector 24 is provide at an end of the universal cord and is detachably connected to the light source 7 and the control device 8.

The bending control unit 3 is an external unit that is detachably connected to the operation portion 22 and rotates the knob 222. As illustrated in FIG. 2, the bending control unit 3 includes a rotation controller 31 and a rotation state detector 32.

The rotation controller 31 controls a rotation state of the knob 222. The rotation state of the knob 222 corresponds to a bending direction and a bending amount of the knob 222. In other words, the rotation controller 31 controls a bending state of the bendable portion 212. The bending state of the bendable portion 212 corresponds to a bending direction and a bending amount of the bendable portion 212.

The rotation state detector 32 detects a rotation state of the knob 222. In other words, the rotation state detector 32 detects the bending state of the bendable portion 212 and corresponds to a bending state detection unit. The rotation state detector 32 outputs a signal representing the detected rotation state of the knob 222 to the control device 8.

The distance measurement unit 4 is what is referred to as a millimeter wave radar module that measures a distance between the insertion portion 21 and an object by transmitting and receiving millimeter waves or submillimeter waves ("millimeter waves/submillimeter waves" below). The distance measurement unit 4 outputs a signal representing the measured distance to the control device 8.

The flexible waveguide 5 is a waveguide that is flexible and elongated and whose one end is connected to the distance measurement unit 4. The flexible waveguide 5 propagates millimeter waves/submillimeter waves that are transmitted by the distance measurement unit 4 from the one end to the other end of the flexible waveguide 5 and emits the millimeter waves/submillimeter waves from the other end to the outside of the flexible waveguide 5 and propagates the millimeter waves/submillimeter waves that are reflected from the object from the other end toward the one end of the flexible waveguide 5 (toward the distance measurement unit 4). The millimeter waves are radio waves having a wavelength of approximately 1 mmm to 10 mmm (for example, around 4 mm one used for a car radar) and the submillimeter waves are radio waves having a wavelength of approximately 0.1 mmm to 1 mmm. In the first embodiment, the flexible waveguide 5 is removably inserted into the channel 214 from the insertion port 223. As illustrated in FIG. 2, the flexible waveguide 5 includes a core 51 and an outer conductor 52.

The core 51 consists of a rod-shaped dielectric that is extended in a state such that the permittivity is constant in a longitudinal direction of the flexible waveguide 5.

The outer conductor 52 is a conductor that is provided on an outer circumference of the core 51 and that is formed by braiding filament yarns into a braid.

The display 6 is a display device, such as a liquid crystal display (LCD) or an electro luminescence (EL) display, and displays a given image under the control of the control device 8.

The light source 7 emits illumination light. The illumination light that is emitted from the light source 7 is advanced to the inside of the body from the distal end of the insertion portion 21 via the connector 24, the universal cord 23, the operation portion 22, the aforementioned light guide that is drawn in the insertion portion 21, and the illumination optical system.

The control device 8 includes a central processing unit (CPU), a field-programmable gate array (FPGA), or the like, and generally controls operations of the bending control unit 3, the distance measurement unit 4, the display 6, and the light source 7. As illustrated in FIG. 2, the control device 8 includes a controller 81 and a storage 82.

The controller 81 consists of the CPU, the FPGA, or the like, and controls operations of the bending control unit 3, the distance measurement unit 4, the display 6, and the light source 7 by executing a given program that is stored in the storage 82.

For example, the controller 81 generates an endoscopic image by performing given processing on the image signal that is input via the aforementioned signal line from the above-described imaging unit. The controller 81 controls operations of the display 6 and causes the display 6 to display the endoscopic image, etc.

Note that a function of controlling the bending control unit 3 and the distance measurement unit 4 in the controller 81 will be described in "Operations of Endoscope System" described below.

The storage 82 stores the program that is executed by the controller 81, data necessary for a process performed by the controller 81, etc.

Note that, in the first embodiment, the light source 7 and the control device 8 are configured independently; however, the light source 7 and the control device 8 may be provided integrally in a single casing.

Operations of Endoscope System

Operations of the above-described endoscope system 1 will be described next.

Note that, it is assumed below that the bending control unit 3 that is an external unit is in a state of being mounted on the operation portion 22 (the state illustrated in FIG. 2) and the flexible waveguide 5 is in a state of being inserted into the channel 214 from the insertion port 223 (the state illustrated in FIG. 2).

The controller 81 outputs a control signals ("first control signal" below) to each of the bending control unit 3 and the distance measurement unit 4 in order to search for an appropriate bending state of the bendable portion 212, for example, in response to a user operation on the operation portion 221.

The bending control unit 3 operates as described below according to the first control signal from the controller 81.

The rotation controller 31 causes the knob 222 to bend sequentially in various bending directions and in various bending amounts. Accordingly, the bendable portion 212 bends sequentially in various bending directions and in various bending amounts.

The rotation state detector 32 sequentially detects rotation states of the knob 222 when the rotation controller 31 is executing control on the rotation state of the knob 222. The rotation state detector 32 sequentially outputs signals representing the detected rotation sates of the knob 222 to the control device 8.

On the other hand, the distance measurement unit 4 operates as described below according to the first control signal from the controller 81.

When the rotation controller 31 is executing control on the rotation state of the knob 222, the distance measurement unit 4 sequentially measures distances each between the insertion portion 21 and the object that is positioned beyond a distal end side of the flexible waveguide 5 by transmitting and receiving millimeter waves/submillimeter waves via the flexible waveguide 5. The distance measurement unit 4 sequentially outputs signals representing the measured distances to the control device 8.

The controller 81 sequentially generates sets of associated information by associating the rotation states of the knob 222 based on the signals that are sequentially output from the rotation state detector 32 and the distances based on the signals that are sequentially output from the distance measurement unit 4 and causes the storage 82 to store the sets of associated information. For example, the distance that is associated with the rotation state of the knob 222 contained in a given set of associated information corresponds to the distance between the insertion portion 21 and the object that is measured by the distance measurement unit 4 when the knob 222 is in the rotation state.

The controller 81 refers to all the sets of associated information stored in the storage 82 and extracts (determines), from all the sets of associated information, a set of associated information with the largest distance as a set of associated information containing the appropriate bending state. Thereafter, the controller 81 outputs a control signal ("second control signal" below) representing the rotation state ("appropriate rotation state" below) of the knob 222 contained in the extracted set of associated information to the bending control unit 3.

The bending control unit 3 operates as described below according to the second control signal from the controller 81.

The rotation controller 31 controls the rotation state of the knob 222 until the rotation state detector 32 detects that the rotation state of the knob 222 enters the appropriate rotation state based on the second control signal. When the rotation state of the knob 222 enters the appropriate rotation state, the bending state of the bendable portion 212 enters the appropriate bending state. As described above, the controller 81 corresponds to a bending state determination unit.

Figure 3:
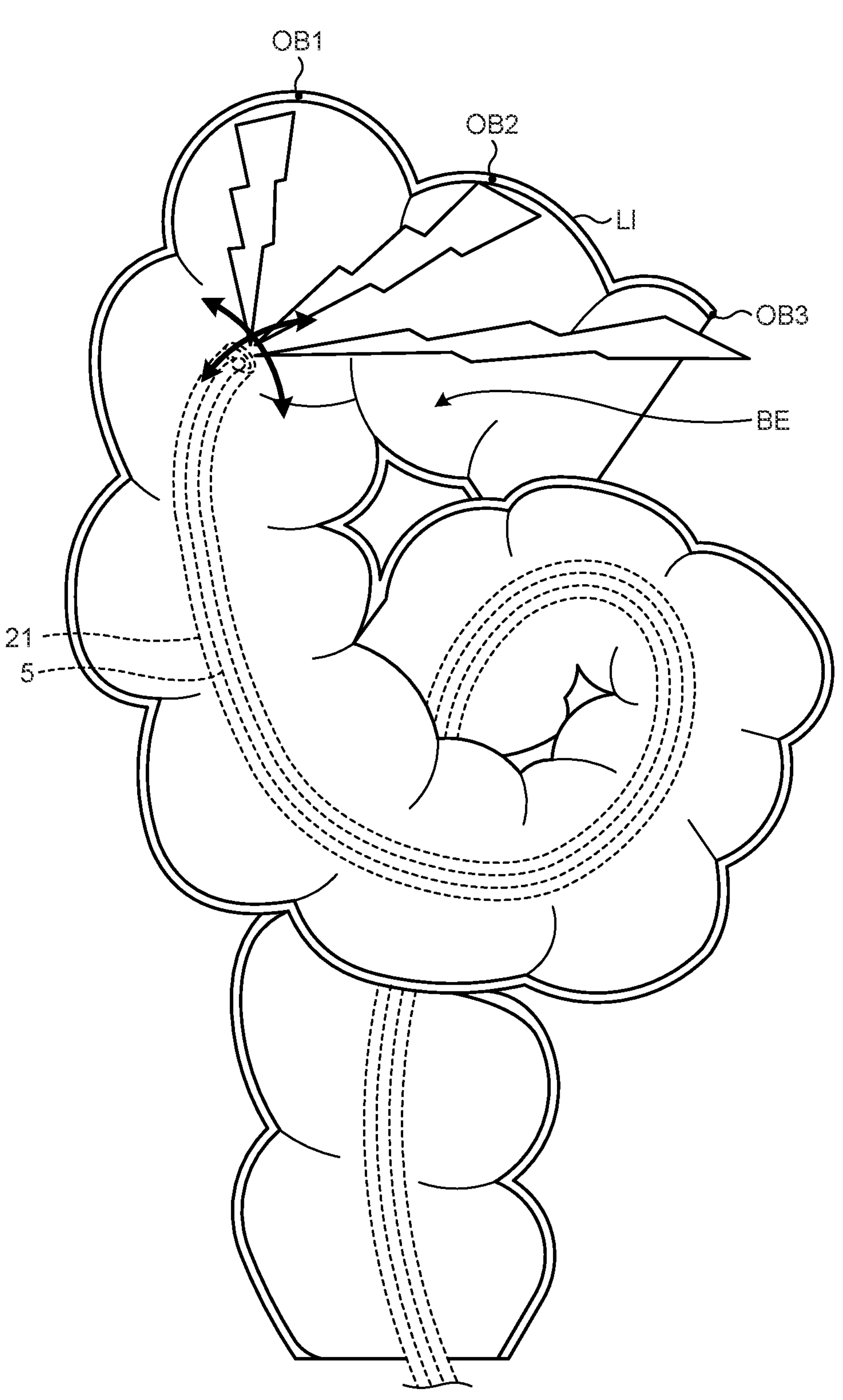
FIG. 3 is a diagram for describing an operation of the endoscope system.

FIG. 3 is a diagram for describing an operation of the endoscope system 1. Specifically, FIG. 3 is a diagram illustrating the state in which the insertion portion 21 is inserted into a large intestine LI.

It is assumed that, as illustrated in FIG. 3, the insertion portion 21 is inserted into the large intestine LI and the distal end of the insertion portion 21 is positioned in a bent portion BE in the large intestine LI. In this case, because of the above-described operation of the endoscope system 1, the distal end of the insertion portion 21 turns in a direction described below. Note that, for the convenience of description, it is assumed that the distance measurement unit 4 measures each of three distances to objects OB1 to OB3 (FIG. 3) from the insertion portion 21.

In other words, the largest distance among the distances between the distal end of the insertion portion 21 and the objects OB1 to OB3 is the distance between the distal end of the insertion portion 21 and the object OB3. Thus, because of the above-described operation of the endoscope system 1, the bending state of the bendable portion 212 enters the appropriate bending state and accordingly the distal end of the insertion portion 21 turns to the object OB3.

According to the first embodiment, the following effect is achieved.

The endoscope system 1 according to the first embodiment employs the bending control unit 3, the distance measurement unit 4, the flexible waveguide 5, and the controller 81.

It is thus possible to automatically set the bending state of the bendable portion 212 at the appropriate bending state and turn the distal end of the insertion portion 21 in an intended direction of insertion of the insertion portion 21.

Thus, according to the endoscope system 1 according to the first embodiment, it is possible to increase operability.

Particularly because the bending control unit 3 consists of the external unit and the flexible waveguide 5 is removably inserted into the channel 214 from the insertion port 223, a general-purpose endoscope 2 is usable as the endoscope 2. In other words, it is unnecessary to add a special configuration to the endoscope 2 and the configuration of the endoscope 2 is not made complex.

Second Embodiment

A second embodiment will be described next.

In the following description, the same components as those of the above-described first embodiment are denoted with the same reference numerals as those of the first embodiment and detailed description thereof will be omitted or simplified.

In the above-described first embodiment, an appropriate bending state of the bendable portion 212 is searched for by using millimeter waves/submillimeter waves.

On the other hand, in the second embodiment, an abnormal site in a living body is detected by using millimeter waves/submillimeter waves. A bleeding site in a lumen or a tumor occurrence site on a wall of a lumen can be exemplified as the abnormal site here.

Figure 4:
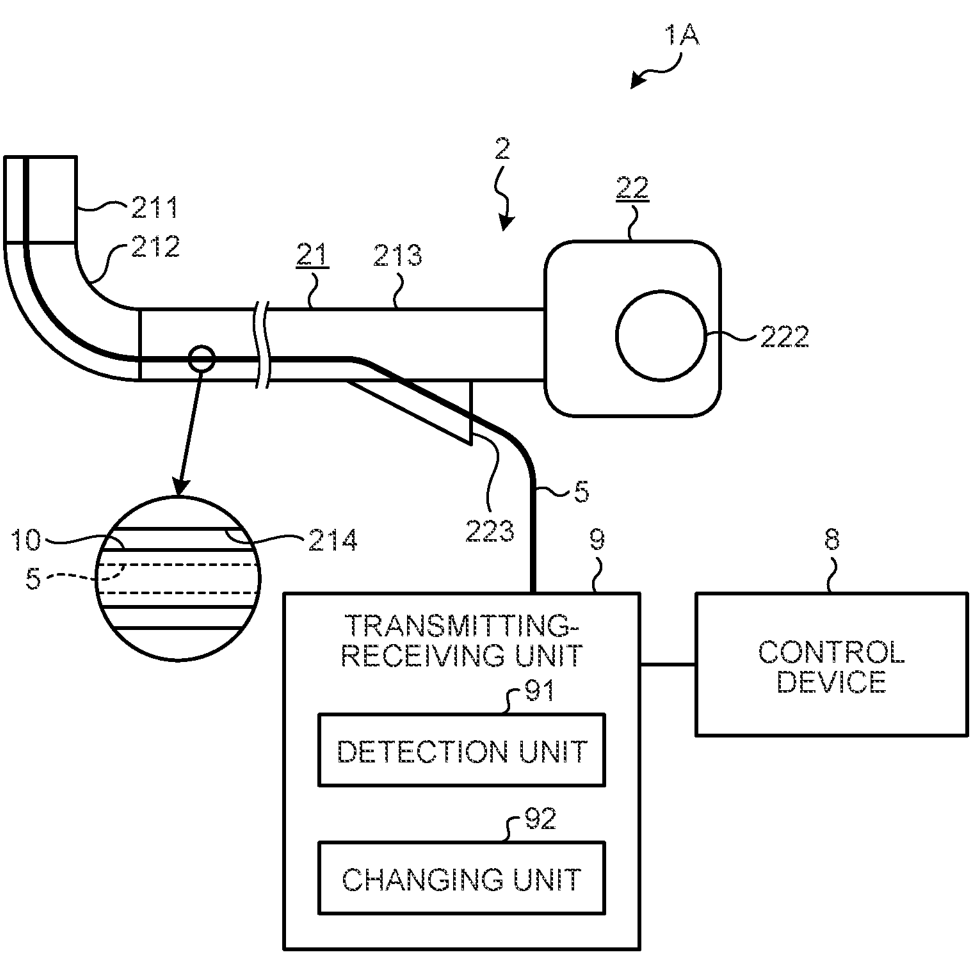
FIG. 4 is a diagram illustrating a configuration of a relevant part of an endoscope system according to a second embodiment.

FIG. 4 is a diagram illustrating a configuration of a relevant part of an endoscope system 1A according to the second embodiment.

In the endoscope system 1A according to the second embodiment, as illustrated in FIG. 4, the bending control unit 3 in the endoscope system 1 according to the above-described first embodiment is omitted and a transmitting-receiving unit 9 is employed instead of the distance measurement unit 4 in the endoscope system 1 according to the above-described first embodiment.

One end of the flexible waveguide 5 is connected to the transmitting-receiving unit 9. As illustrated in FIG. 4, the transmitting-receiving unit 9 includes a detection unit 91 and a changing unit 92.

The detection unit 91 transmits and receives millimeter waves/submillimeter waves via the flexible waveguide 5 and compares the transmitted millimeter waves/submillimeter waves and the received millimeter waves/submillimeter waves. The millimeter waves/submillimeter waves are the same millimeter waves/submillimeter waves as those described in the above-described first embodiment. The detection unit 91 detects an abnormal site in the living body based on a change in the state of the millimeter waves/submillimeter waves between the transmitted millimeter waves/submillimeter waves and the received millimeter waves/submillimeter waves. For example, an attenuation rate of the millimeter waves/submillimeter waves and a change in the wavelength of the millimeter waves/submillimeter waves can be exemplified as the state of the millimeter waves/submillimeter waves. The detection unit 91 outputs a signal representing a position of the detected abnormal site to the control device 8.

By using a tube 10 (refer to FIG. 5) into which the flexible waveguide 5 is inserted, the changing unit 92 changes a direction of the other end of the flexible waveguide 5 that is exposed from the distal end of the insertion portion 21 to the outside.

Figure 5:
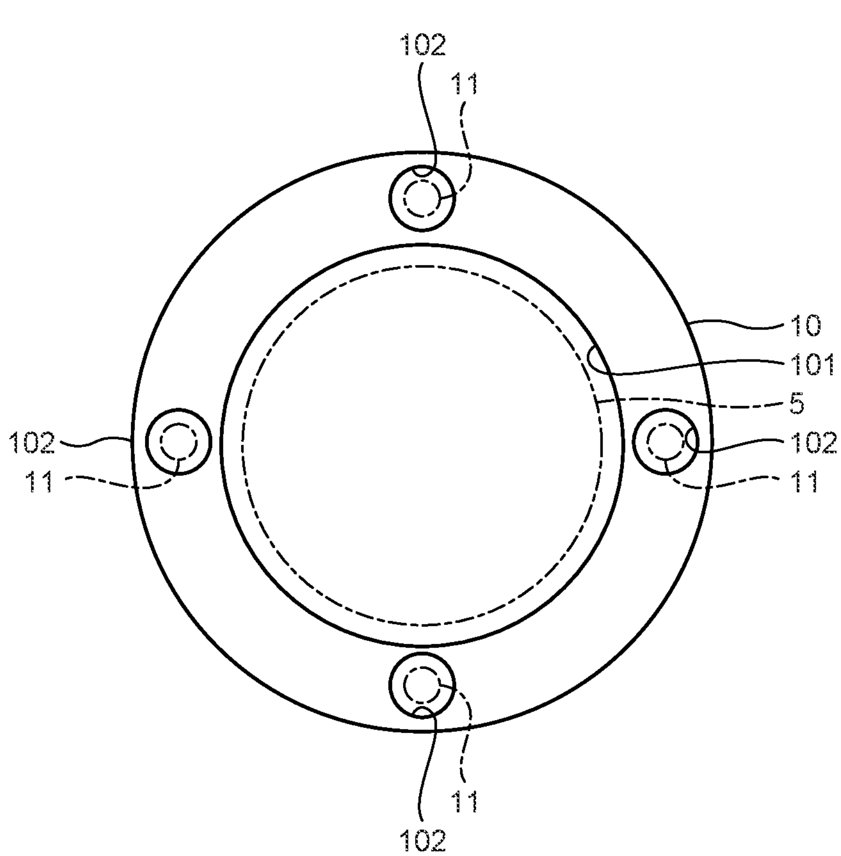
FIG. 5 is a diagram illustrating a configuration of a tube.

FIG. 5 is a diagram illustrating a configuration of the tube 10. Specifically, FIG. 5 is a cross-sectional view of the tube 10 taken along a plane orthogonal to a longitudinal direction of the tube 10.

The tube 10 is a tube that is flexible and has a total length approximately equal to that of the flexible waveguide 5. As illustrated in FIG. 5, the tube 10 is provided with a first through-hole 101 and four second through-holes 102.

As illustrated in FIG. 5, the first through-hole 101 is a hole that is positioned at the center on the cross-section of the tube 10 and that penetrates from one end to the other end of the tube 10. The flexible waveguide 5 is inserted into the first through-hole 101.

As illustrated in FIG. 5, the four second through-holes 102 are holes that surrounds the first through-hole 101 on the cross-section of the tube 10, that are positioned in positions in which second through-holes 102 are rotationally symmetric at 90 degrees on a center axis of the tube 10, and that penetrate from the one end to the other end of the tube 10. Wires 11 made of metal or resin are inserted into the four second through-holes 102, respectively. Distal end portions of the wires 11 (ends on a side distant from the transmitting-receiving unit 9) are fixed to the tube 10.

The changing unit 92 pulls the four wires 11 under the control of the controller 81, thereby changing the direction of the other end of the flexible waveguide 5 containing the tube 10.

When the changing unit 92 is executing control on an orientation of the other end of the flexible waveguide 5, the detection unit 91 detects an abnormal site in the living body as described above. The detection unit 91 outputs a signal representing a positon of the detected abnormal site to the control device 8. Accordingly, the control device 8 generates an endoscopic image in which the position of the abnormal site based on the signal discriminated from other positions, and causes the display 6 to display the endoscopic image.

According to the above-described second embodiment, the following effect is achieved.

The endoscope system 1A according to the second embodiment employs the transmitting-receiving unit 9 described above.

It is thus possible to easily detect an abnormal site in the living body, such as a bleeding site in a lumen or a tumor occurrence site on a wall of a lumen, using a simple configuration.

Other Embodiments

Modes for carrying out the disclosure have been described; however, the disclosure should not be limited only to the above-described first end second embodiments.

In the above-described first embodiment, the configuration of detecting an abnormal site in a living body may be employed as in the above-described second embodiment. In other words, in the above-described first embodiment, at least one of the detection unit 91 and the changing unit 92 that constitute the transmitting-receiving unit 9 described in the second embodiment may be employed.

In the above-described second embodiment, the changing unit 92 may be omitted and the bending control unit 3 described in the above-described first embodiment may be employed. In other words, while the rotation controller 31 is executing control on the rotation state of the knob 222, the detection unit 91 detects an abnormal site in the living body.

In the above-described first and second embodiments, at least part of the flexible waveguide 5 may be incorporated in the insertion portion 21.

In the above-described first embodiment, a notification unit may make a notification of information representing an appropriate bending state that is determined by the controller 81.

For example, the display 6, an indicator (not illustrated in the drawings), a speaker, or the like, can be exemplified as the notification unit.

The display 6 and the aforementioned indicator make a visible notification of the information representing the appropriate bending state that is determined by the controller 81.

Specifically, the display 6 corresponds to a monitor and displays the information as an image. On the other hand, the indicator has, for example, a configuration in which a plurality of light emitting diodes (LEDs), or the like, are arranged in parallel in each of the up-down and left-right directions and is provided adjacently to the display 6. By turning the LEDs arranged in the up-down and left-right directions on, the indicator makes a notification of an appropriate bending state (a bending direction and a bending amount).

The speaker makes an audio notification of the information representing the appropriate bending state that is determined by the controller 81.

In the first end second embodiments described above, the endoscope system is used in the medical fields; however, embodiments are not limited thereto and the endoscope system may be used in the industrial fields.

According to the endoscope system according to the disclosure, it is possible to increase operability.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:

an endoscope including an insertion portion configured to be inserted into a subject;

a distance sensor configured to measure a distance between the insertion portion and an object by transmitting and receiving millimeter waves or submillimeter waves; and a flexible waveguide that has one end that is connected to the distance sensor and another end that is exposed to outside from a distal end of the insertion portion, the flexible waveguide being configured to propagate the millimeter waves or the submillimeter waves transmitted and received by the distance sensor, wherein the flexible waveguide is removably inserted into a channel that is extended from a proximal end side of the endoscope to a distal end of the insertion portion.

2. An endoscope system comprising:

an endoscope including an insertion portion configured to be inserted into a subject;

a distance sensor configured to measure a distance between the insertion portion and an object by transmitting and receiving millimeter waves or submillimeter waves; and a flexible waveguide that has one end that is connected to the distance sensor and another end that is exposed to outside from a distal end of the insertion portion, the flexible waveguide being configured to propagate the millimeter waves or submillimeter waves transmitted and received by the distance sensor, wherein the insertion portion includes a bendable portion that is provided in part of the insertion portion in a longitudinal direction of the insertion portion and that is configured to bend, and the endoscope system further comprises a controller comprising hardware, the controller being configured to:

receive a signal indicating an initial bending state of the bendable portion;

receive, from the distance sensor, a signal indicating the distance between the insertion portion and the object; and determine a target bending state of the bendable portion based on the distance and the initial bending state of the bendable portion.

3. The endoscope system according to claim 2, wherein at least part of the flexible waveguide is incorporated in the insertion portion.

4. The endoscope system according to claim 2, wherein the controller is further configured to cause the bendable portion to bend based on the target bending state of the bendable portion.

5. The endoscope system according to claim 4, wherein the endoscope includes an operation portion configured to receive a user operation, the operation portion includes a knob that is rotatable according to the user operation and that is configured such that a rotation of the knob causes the bendable portion to bend, and the controller is configured to output a signal to rotate the knob.

6. The endoscope system according to claim 2, further comprising a notification unit that is configured to make a notification of the target bending state of the bendable portion.

7. The endoscope system according to claim 6, wherein the notification unit is further configured to make a visible notification of the target bending state of the bendable portion.

8. The endoscope system according to claim 7, wherein the notification unit includes a monitor displaying, as an image, the target bending state of the bendable portion.

9. The endoscope system according to claim 6, wherein the notification unit is further configured to make an audio notification of the target bending state of the bendable portion.

* * * * *